United States Patent [19]
Luber et al.

[11] Patent Number: 5,143,058
[45] Date of Patent: Sep. 1, 1992

[54] FOOT AND LEG SPLINT

[75] Inventors: George H. Luber, Tampa; Donna B. Mann, St. Petersburg, both of Fla.

[73] Assignee: Care Co. Medical Products, Inc., Tampa, Fla.

[21] Appl. No.: 609,711

[22] Filed: Nov. 6, 1990

[51] Int. Cl.⁵ .......................... A61F 3/00; A61F 5/04
[52] U.S. Cl. ........................................................ 602/28
[58] Field of Search ................ 128/80 E, 80 R, 87 R, 128/88, 89, 166, 882, 84 A, 84 B

[56] References Cited

U.S. PATENT DOCUMENTS

| | | | |
|---|---|---|---|
| 27,957 | 4/1974 | Larson | 128/89 |
| D. 33,447 | 11/1900 | Sadler | D24/192 |
| D. 257,594 | 12/1980 | Finnieston | D24/64 |
| D. 268,365 | 2/1983 | Malkin | D24/64 |
| D. 270,284 | 8/1983 | Lindh | D24/64 |
| 433,227 | 7/1990 | Beacock | 128/90 |
| 1,332,047 | 2/1920 | Lasher | 128/80 E |
| 2,523,606 | 9/1950 | Young | 128/90 |
| 2,847,991 | 8/1958 | Andrews | 128/80 E |
| 2,871,851 | 2/1959 | Swanson | 128/80 E |
| 2,911,657 | 8/1959 | Streeter, III | 5/327 |
| 2,986,747 | 6/1961 | Posey | 128/80 E |
| 3,263,679 | 8/1966 | Hass | 128/83.5 |
| 3,345,654 | 2/1966 | Noble | 5/319 |
| 3,351,055 | 11/1967 | Gottfried | 128/87 |
| 3,523,526 | 8/1970 | Phelps | 128/80 |
| 3,527,209 | 9/1970 | Baker | 128/80 E |
| 3,584,622 | 6/1971 | Domenico | 128/166 |
| 3,589,359 | 6/1971 | Hill | 128/80 |
| 3,606,884 | 9/1971 | Peter | 128/80 |
| 3,618,946 | 11/1971 | Lee | 128/80 R |
| 3,698,389 | 10/1972 | Guedel | 128/77 |
| 3,713,437 | 1/1973 | Wiedmer | 128/25 |
| 3,892,231 | 7/1975 | Tummillo | 128/80 |
| 3,916,886 | 11/1975 | Rogers | 128/80 E |
| 3,976,059 | 8/1976 | Lonardo | 128/80 E |
| 4,061,138 | 11/1977 | Bernstein | 128/82 |
| 4,177,583 | 12/1979 | Chapman | 36/77 |
| 4,289,122 | 9/1981 | Mason | 128/80 |
| 4,454,871 | 6/1984 | Mann | 128/80 |
| 4,454,872 | 6/1984 | Brouhard | 128/82 |
| 4,554,912 | 11/1985 | Haberman | 128/80 E |
| 4,566,208 | 1/1986 | Shaffner | 36/110 |
| 4,651,723 | 3/1987 | Satoh | 128/80 E |
| 4,809,687 | 2/1989 | Allen | 128/84 |
| 4,834,078 | 5/1989 | Biedermann | 128/80 |
| 4,841,957 | 6/1989 | Wooten | 128/80 |

FOREIGN PATENT DOCUMENTS 937846 2/1953 Fed. Rep. of Germany .

OTHER PUBLICATIONS

Gemini Medical Products, Jul. 1988.
L'nard Multi-Podus Splint, Jul. 1988.

Primary Examiner—Robert A. Hafer
Assistant Examiner—Michael Brown
Attorney, Agent, or Firm—Laff, Whitesel, Conte & Saret

[57] ABSTRACT

A foot and leg splint has two main elements: a hard plastic shell portion and a flexible boot-like garment assembly which cushions the patient's foot and secures the foot to the shell. The shell has a back section shaped to provide comfortable support for the calf and lower leg of the patient. A first portion of the heel section extends straight downward from the back section with a flat back surface to prevent unwanted rocking or rotation of the patient's foot when the patient is in a prone position. A second portion of the heel section extends horizontally, perpendicular to the first section of the heel to form a squared-off heel and provide a flat surface for supporting the heel when the patient is standing or walking. A plantar section extends forward from the second heel portion and curves upward to support the arch of the patient's foot. A toe protector may be provided to extend forward beyond the plantar section. The boot-like garment assembly is provided with pockets to receive each end of the shell and a strap to extend around behing the heel portion of the shell. The boot-like garment has a fleece-like, soft inner-liner which covers much of the patient's foot and calf, and a canvas outer jacket to envelop the inner-liner and protect the patient's foot. Additional straps may be provided to encircle the patient's ankle and upper calf to secure the patient's foot and leg to the shell.

16 Claims, 6 Drawing Sheets

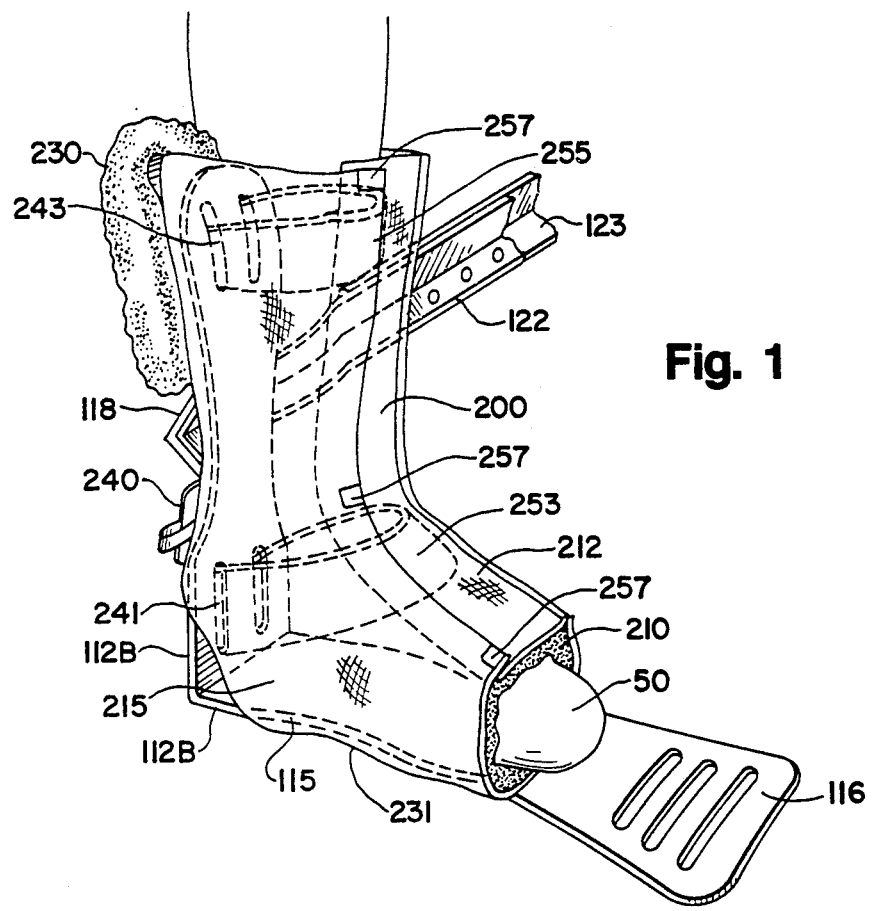
Fig. 1
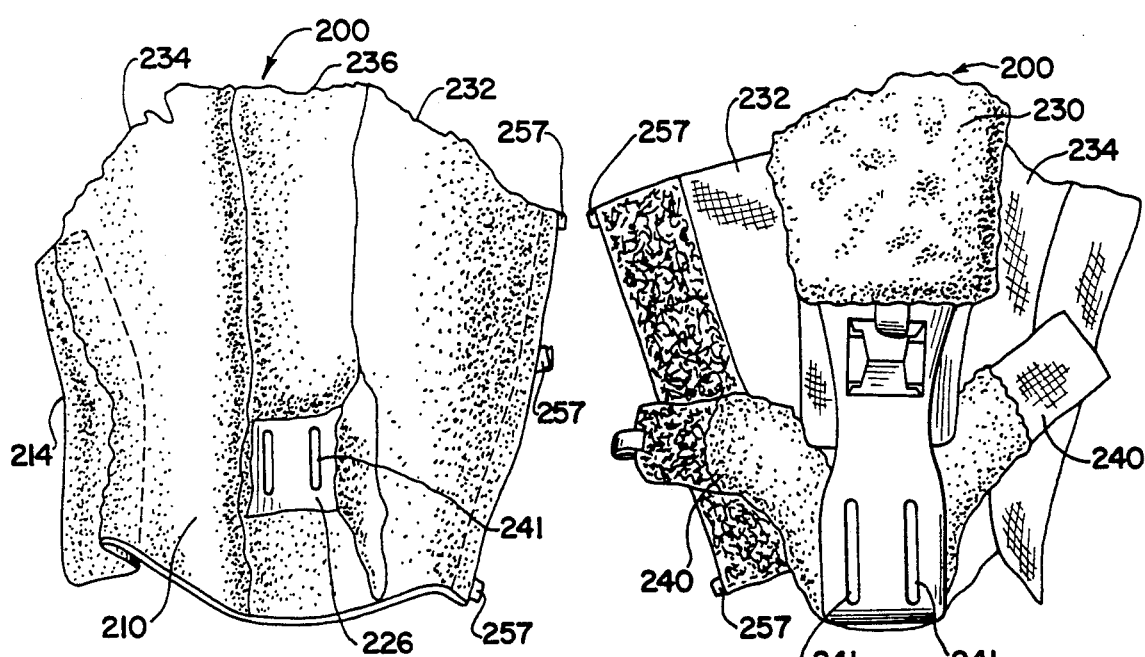
Fig. 10
Fig. 11

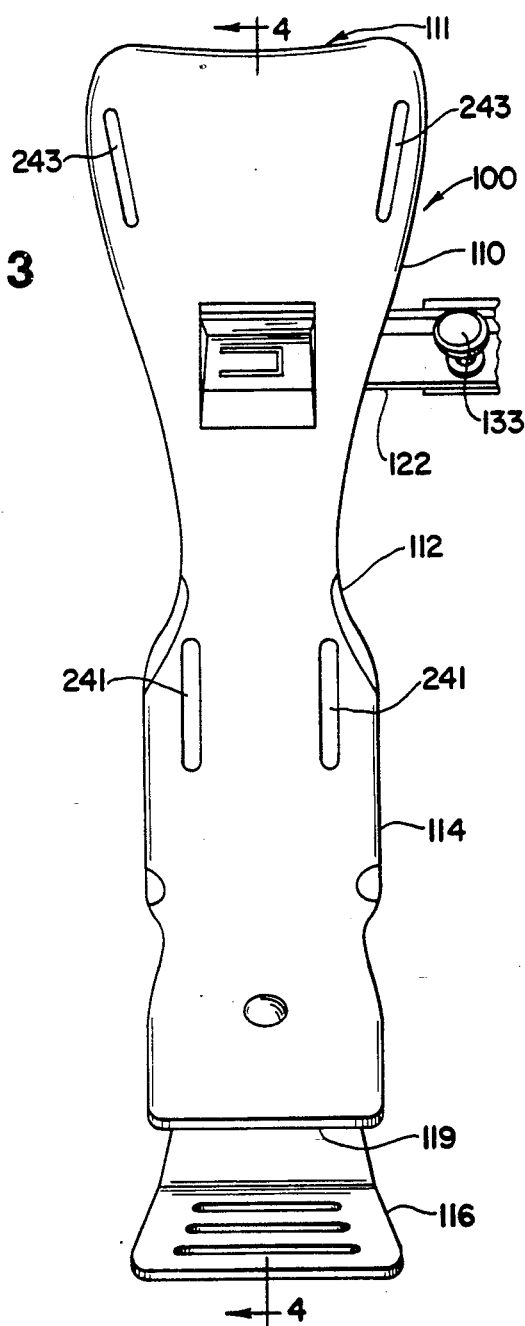
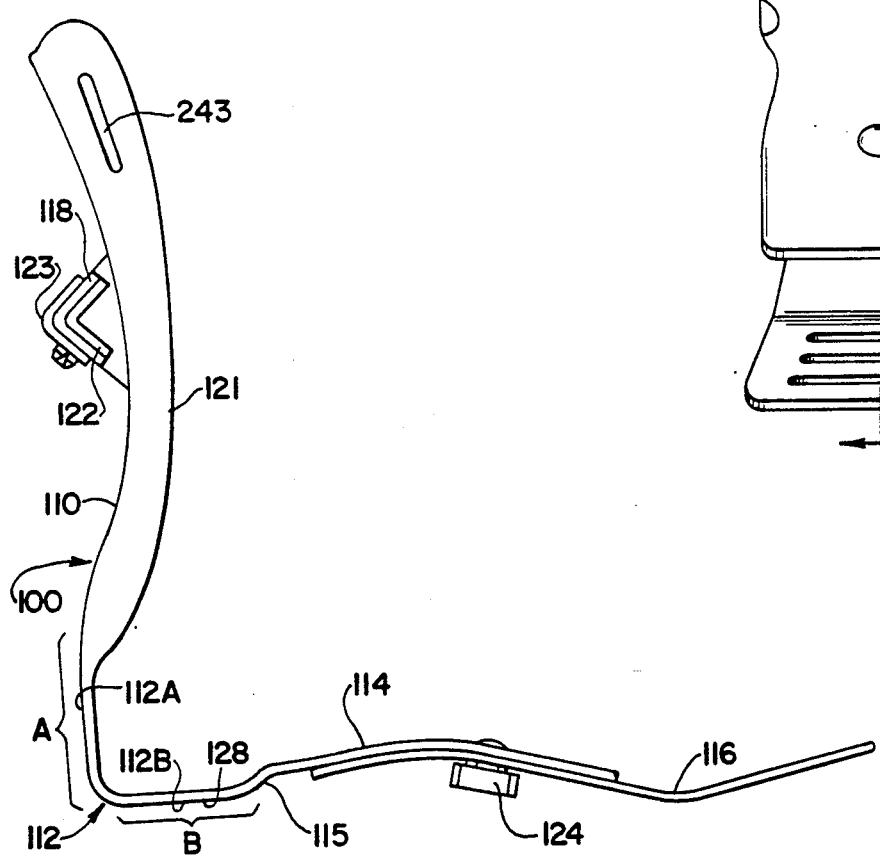

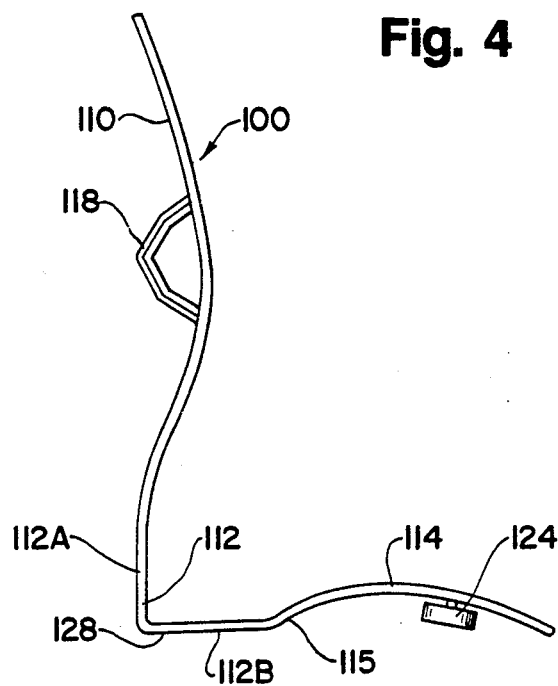
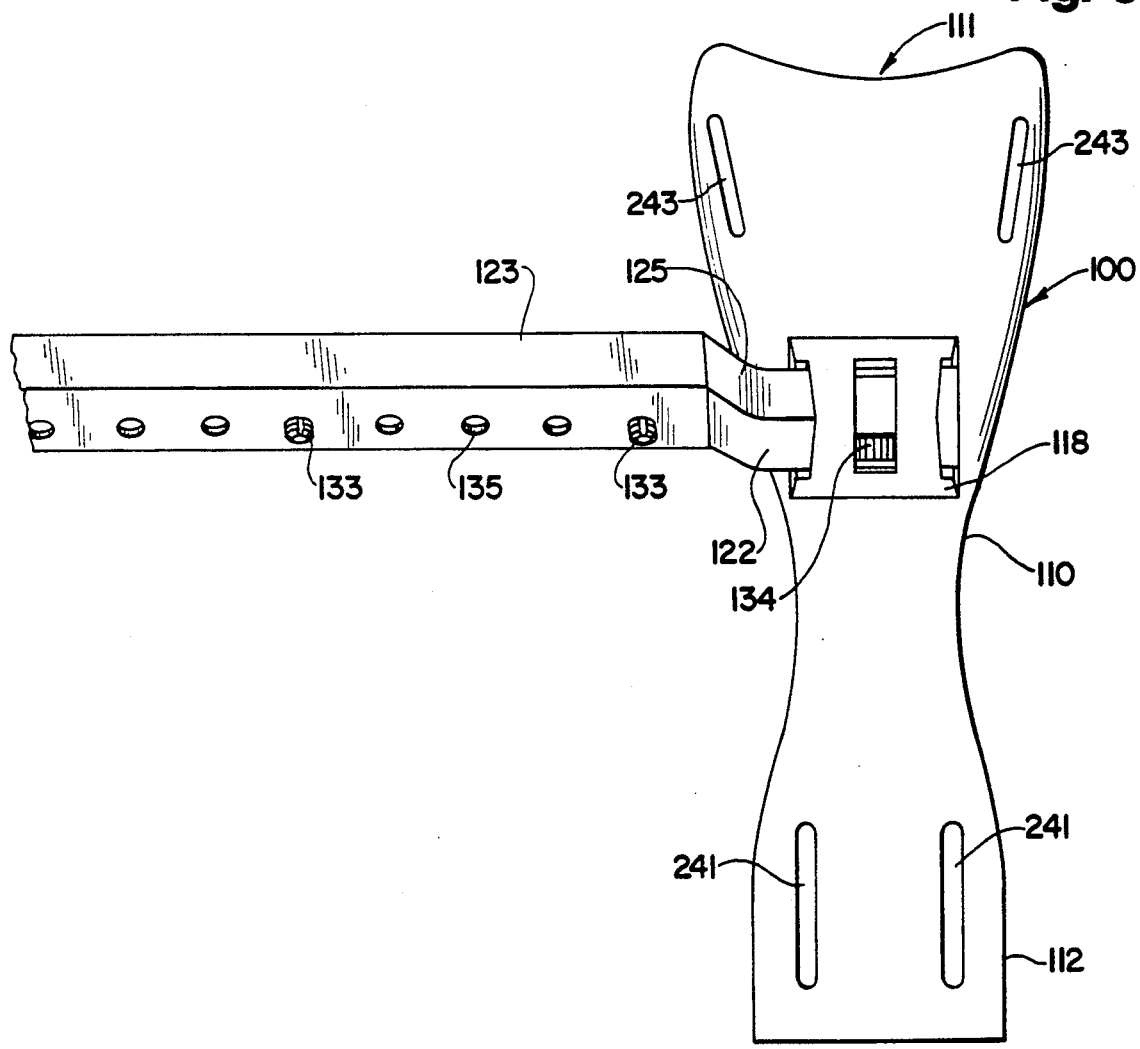

FOOT AND LEG SPLINT

BACKGROUND OF THE INVENTION

This invention relates to splints or braces and more particularly to splints designed to support the lower leg, ankle and foot to prevent foot-drop and other similar conditions that can result from prolonged immobility or bed rest.

A person who must be immobilized or confined to bed for a significant period of time, such as a person who has suffered a stroke or similar disability, may develop a variety of conditions resulting from the weakening of the leg and foot muscles and global tendons, such as foot-drop, knee flexion and inversion or eversion of the foot. Foot-drop results from the weakening or atrophy of the muscles in the foot and lower leg from lack of use. The upper leg muscles and Achilles tendon contract from lack of use, bending the knee joint (called knee flexion) to pull the knee upward and the foot downward. The foot also drops downwardly from its normal position, which is substantially perpendicular to the leg, to a position in which the foot is extended at an obtuse angle to the leg. In addition, when the knee is pulled up, it often will also rotate inward or outward, causing the entire lower leg and foot to rotate in the same direction. Similarly, immobilization can also result in the contraction of the upper or lower tendons in the foot, causing the foot to curve inward or outward (called foot inversion or eversion).

Unless a person can maintain his or her foot in a functional position, i.e. directed at a 90° angle outward from the leg, it is very difficult to stand or walk. Consequently, prolonged bed rest or immobility, without taking the necessary preventive steps, may result in a person's losing the ability to stand or walk. Although such conditions subsequently can be corrected, it is much easier to prevent the conditions in the first place. In addition, when a patient's leg or foot rotates as a result of immobility or prolonged bed rest, bed sores commonly result. As the patient's leg or foot rotates and is pressed downward onto the bed, such sores develop through pressure necrosis at the point of contact with the bed's surface. Moreover, the contracting leg and foot muscles and tendons tend to reduce or cut off circulation to the extremities by increasing the amount of pressure, further contributing to the development of bed sores.

Numerous prior art devices have been designed to prevent or correct foot-drop and other similar conditions, such as the devices shown in U.S. Pat. Nos. 3,976,059; 2,874,991; 3,345,654; 3,527,209; 3,713,437; 3,916,886; 4,289,122; and 4,554,912. Such devices, however, suffer from several design drawbacks, including: lack of stability for standing or walking; rounded surfaces that promote rotation or rocking of the foot when the patient is in a prone position; lack of sufficient flexibility to permit the patient's foot to move against and bend the splint as a form of active exercise; lack of adequate attachment and support means; lack of any provision for preventing the patient's foot or leg from turning to one side or the other while the patient is in a prone position; a design that may injure the upper calf muscles; and protrusions or surfaces along the interior and exterior of the splint which themselves can irritate and thus cause sores on a patient's foot and/or leg.

For example, U.S. Pat. No. 3,976,059 shows a splint with a rounded heel which provides an unstable configuration for standing or walking. U.S. Pat. No. 3,916,886 discloses a splint which employs a strap adjacent the top and flanges along the periphery for attachment to a patient's foot, an arrangement which may not adequately support and secure the lower leg and foot of the patient in the splint.

OBJECTS AND SUMMARY OF THE INVENTION

Accordingly, an object of the present invention is to provide a splint to prevent foot-drop and related conditions (hereinafter collectively referred to as foot-drop) which has a stable configuration for standing and walking.

Another object of the present invention is to provide a splint to prevent foot-drop which reliably secures the patient's lower leg and foot to the splint.

A further object is to provide a splint to prevent foot-drop which provides an efficient means to preclude the patient's foot from rotating or rocking from side to side when the patient is in a prone position.

Yet another object of the present invention is to provide a splint to prevent foot-drop which does not include any protrusions or other surfaces on the interior or exterior of the splint which can irritate or cause sores on a patient's leg or foot.

Still a further object of the invention is to provide a splint to prevent foot-drop which is streamlined in shape and relatively light in weight.

Yet a further object of the invention is to provide a splint which exerts an upward pressure in the range of at least three to six pounds per square inch, and possibly three to eight pounds per square inch, against a patient's foot that is being pulled downward against the splint.

Another object of the invention is to provide a splint to prevent the leg muscles of a patient from contracting and causing knee flexion.

Still a further object of the invention is to provide a splint to prevent inversion or eversion of a patient's foot.

Another object of the invention is to provide a splint which is designed to prevent injury to the upper calf muscle.

BRIEF DESCRIPTION OF THE DRAWINGS

A preferred embodiment of the invention is shown in the attached drawings, wherein:

FIG. 1 is a front perspective view of a foot and leg splint according to the present invention, showing a patient's leg secured therein;

FIG. 2 is a side elevational view of the shell of the foot and leg splint according to the present invention;

FIG. 3 is a front elevational view of the shell of FIG. 2.

FIG. 4 is a cross sectional view of the shell of FIGS. 2 and 3 taken along the lines 4—4 of FIG. 3, looking in the direction of the arrows;

FIG. 5 is a rear elevational view of the shell of FIGS. 2–4;

FIG. 10 is a front elevational view of a soft garment for the foot splint of FIG. 1, shown in an open and unsecured position;

FIG. 11 is a rear elevational view of the soft garment of FIG. 10, shown in an opened and unsecured position.

DETAILED DESCRIPTION OF THE PREFERRED EMBODIMENT

Figure 6:
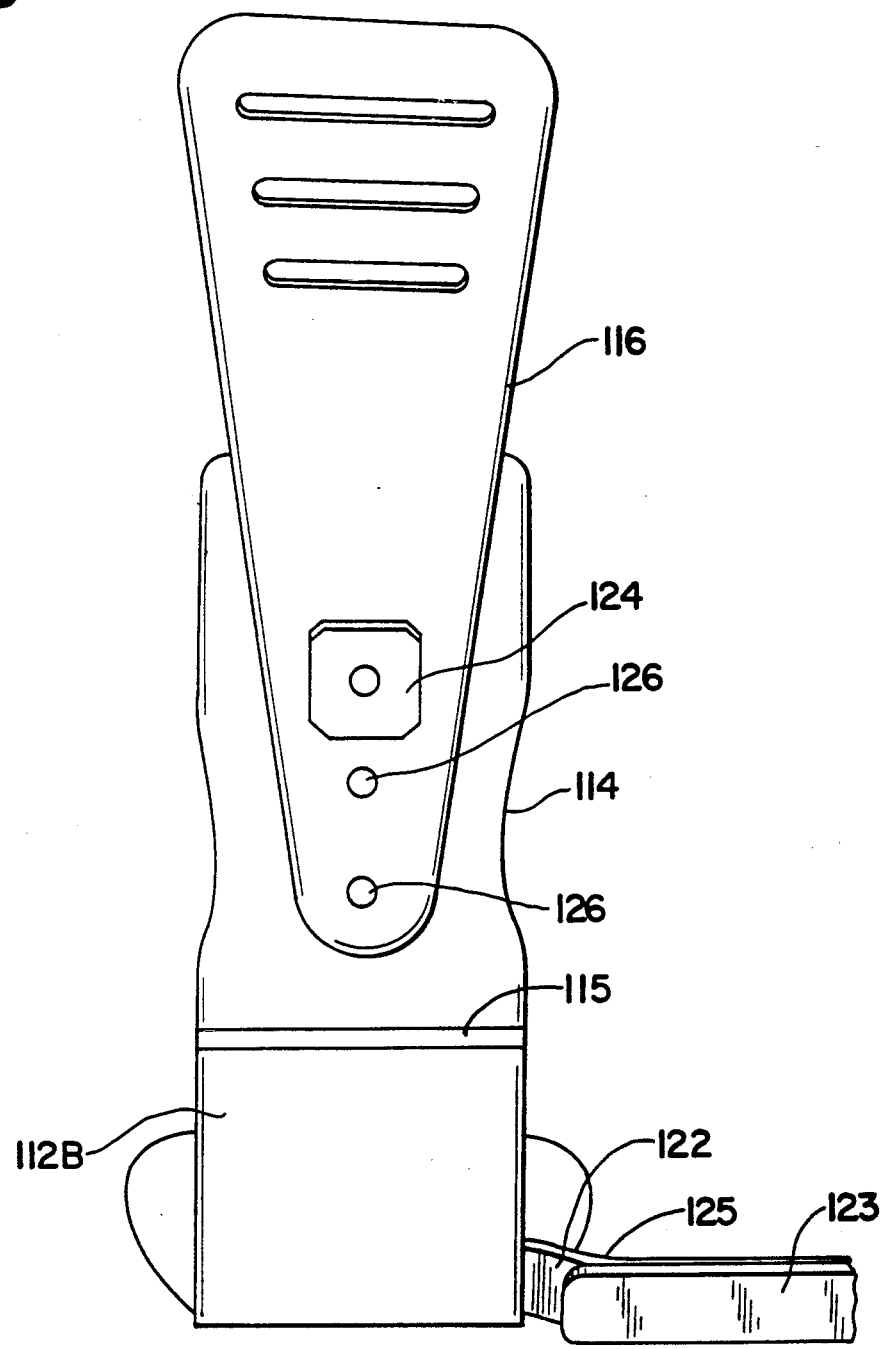
FIG. 6 is a bottom plan view of the shell of FIGS. 2–5 with the toe-protector, lateral snap-in bar and abductor bar attached.
Figure 7:
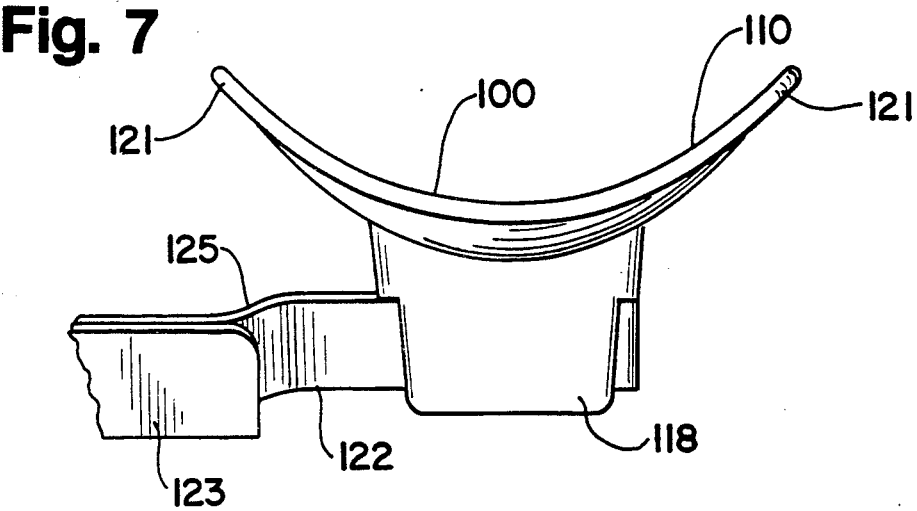
FIG. 7 is a partial top plan view of the shell of FIGS. 2–6 from which the bottom portion of the shell is omitted.
Figure 8:
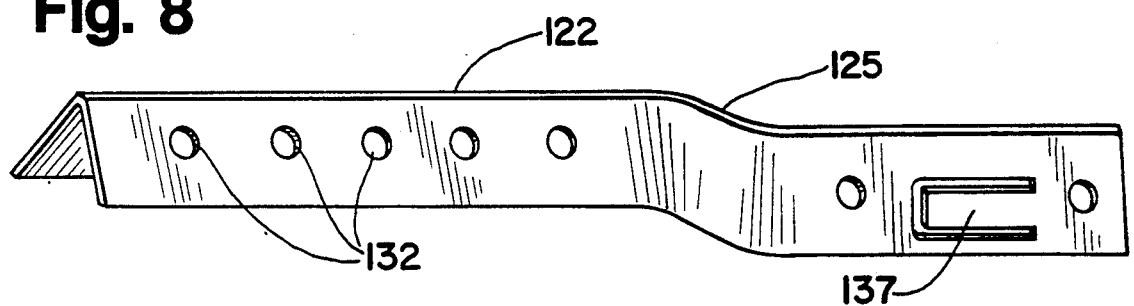
FIG. 8 is a perspective view of a lateral snap-in bar for the foot splint of FIG. 1.
Figure 9:
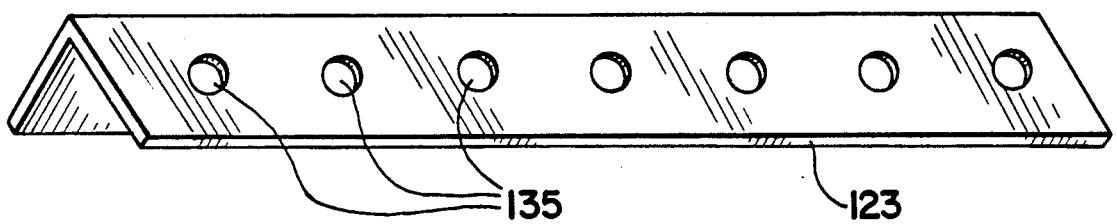
FIG. 9 is a perspective view of an abductor bar for the foot splint of FIG. 1.
Figure 12:
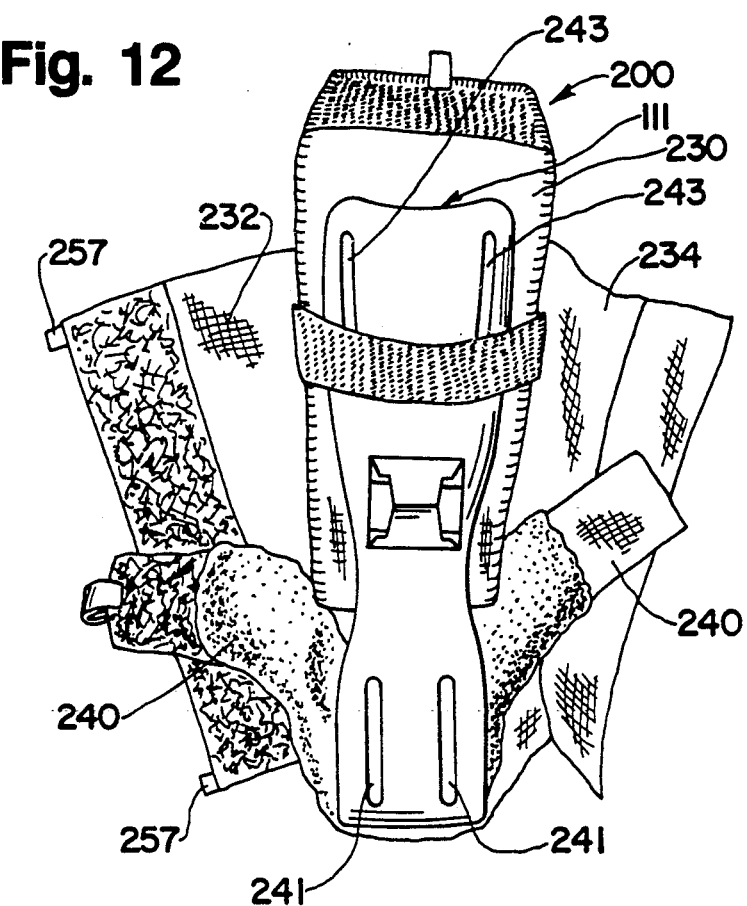
FIG. 12 is a rear elevational view of the soft garment of FIG. 10, shown in an opened and unsecured position with the upper flap in an extended and opened position.
Figure 13:
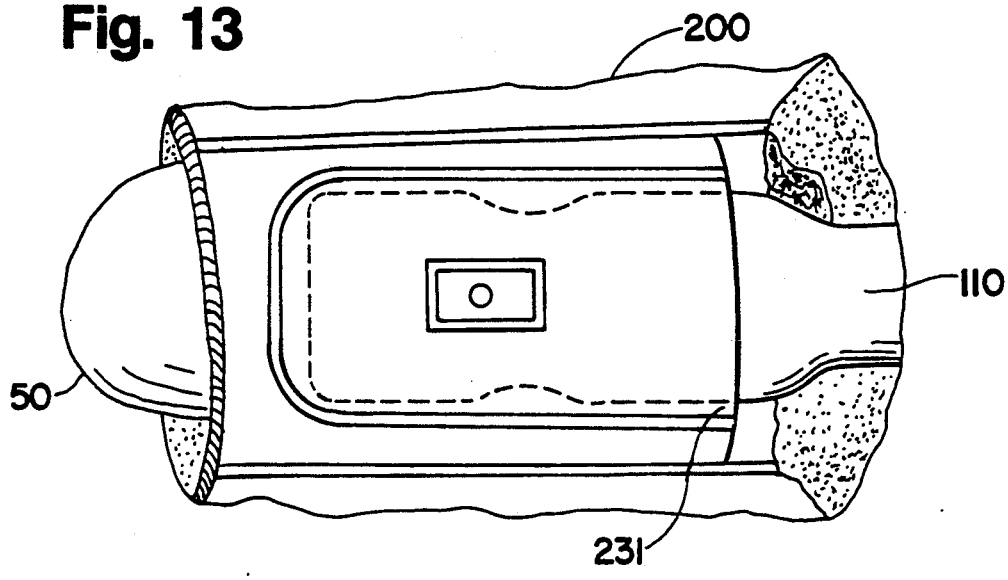
FIG. 13 is a partial bottom plan view of the shell of FIGS. 2-5 with the soft garment of FIGS. 10-12 secured thereto.

The new splint is generally shown in FIGS. 1-13. FIG. 1 is an overall view of the splint with a patient's foot 50 attached thereto. The splint comprises two main elements: a hard plastic shell portion 100 (FIGS. 1-7); and a flexible boot-like garment assembly 200 (FIGS. 1 and 10-13) which cushions the patient's foot and secures the foot to the shell 100.

As shown in FIGS. 1 to 3, the shell 100 has a back section 110, a heel section 112, and a plantar section 114. The back section 110 supports the rear portion (i.e. the calf, etc.) of the patient's lower leg. Section 110 is shaped in a gentle curve (see FIG. 4) that extends outward toward the middle of the patient's calf and then in a reverse direction away from the patient's leg at its lower end where it leads into heel section 112. This curved shape provides comfortable support for the calf and lower leg. The sides of section 110 are curved somewhat inward to form flange 121 (FIGS. 2 and 7) to provide a cradle for supporting the calf and lower leg.

The height and shape of the leg or calf section of some prior art devices sometimes contributed to the injury or irritation of a patient's calf muscle. The present invention overcomes this disadvantage by shortening the height of section 110 and by forming the upper edge 111 of section 110 as a concave or downward curve.

A first or upper portion 112A of heel section 112 (FIG. 2) extends straight downward a predetermined distance A from section 110. A second or lower portion 112B of heel section 112 extends horizontally a predetermined distance B from portion 112A to section 115, perpendicular to portion 112A to form the bottom of heel section 112. Portions 112A and 112B thus form a squared-off heel and provide flat surfaces for supporting the heel when the patient is respectively in a prone position, or standing or walking. Heel portion 112B terminates in an upward extending section 115.

When the patient is in a prone position, lying on his or her back, the patient's heel is supported against the bed or other surface by the flat back surface of upper portion 112A, which helps to prevent unwanted rocking or disrotation of the patient's foot.

Likewise, the flat underside of lower heel portion 112B provides a stable surface for standing or walking, and preferably is provided with a non-slip bottom surface 128. Both the front and back surfaces of portion 112A and the underside of portion 112B overcome certain disadvantages of prior art devices that had rounded heels. Such rounded heels of the prior art devices permitted the patient's foot to rock or rotate when the patient rested in a prone position, and also do not provide a stable configuration for standing or walking.

Plantar section 114 extends forward from section 115 toward the toes. Section 114 curves upward from section 115 to support the arch of the patient's foot, and then slightly downward adjacent the ball of the patient's foot. The front 119 of plantar section 114 is squared off as shown in FIG. 3 so that it presents a straight outer edge or surface.

Shell 100 is constructed from a somewhat flexible material such as polycarbonate, so that downward pressure exerted by a patient's foot will cause the plantar section 114 to flex or bend slightly downwardly. In the preferred embodiment, the plantar section 114 will resist the downward movement or flexing of a patient's foot by exerting an upward counter-pressure of at least three to six pounds per square inch, and possibly three to eight pounds per square inch, against the foot.

An optional toe-protector 116 extends forward beyond the patient's toes to guard them from injury or irritation due to contact with foreign objects (see FIGS. 2, 3 and 6). The toe protector is wider at its outer extremity to increase support and protection for a patient's toes and upper foot. The toe-protector 116 is attached to the plantar portion 114 by an appropriate fastener 124. As shown in FIGS. 2 and 4, the fastener 124 may be a hand-operated bolt so that the user may easily attach or detach the toe-protector. The toe-protector 116 includes a plurality of alternative mounting apertures 126 (FIG. 6) so that the length of the guard extending beyond the plantar portion 114 may be conveniently adjusted. The toe-protector 116 may also be turned to, and secured in, a position extending from either side of splint 100 to raise the side of the patient's foot off the surface of the bed when the patient lies on his or her side. Turning the toe-protector 116 to the side will help to protect the foot from irritating contact with the bed.

To prevent rotation of the patient's leg or foot while he or she is lying in bed, a lateral snap-in bar 122 (shown in FIGS. 3, 6 and 8) may be adjustably installed in a corresponding receptacle 118 (FIGS. 2,4,5 and 7) located on the back section 110 of the splint. The lateral snap-in bar 122 may be installed to point to either the left or right side of the patient, parallel to the floor and perpendicular to the direction in which the patient's toes point. Lateral snap-in bar 122 curves rearwardly away from the back of shell 110 at point 125 (FIGS. 6 and 7) so that the bar 122 will rest in a stable position against the surface of a bed when a patient wearing the splint lies on his or her back in a prone position (see FIGS. 6 and 7). As described below, the curvature of lateral snap-in bar 122 at point 125 also permits a abductor 123 to be attached to lateral snap-in bar 122 and to extend sidewardly behind the shell 110 in a direction opposite that of lateral snap-in bar 122.

If the patient is lying on his or her back, the lateral snap-in bar 122 lies parallel to the surface of the bed, thereby preventing the patient from rotationally displacing his foot or leg in the direction of the bar. In other words, the patient's foot is maintained in an upward-pointing orientation. The bar 122 is removed when the patient desires to stand or walk. The bar 122 has a catch 137 (FIG. 8) for engaging an internal latch mechanism 134 (FIG. 5) when the bar is installed in the receptacle 118.

Receptacle 118 on the back of section 110 and internal latch mechanism 134 provide an efficient and streamlined mechanism for securing lateral snap-in bar 122 to the splint. This design eliminates protrusions or other surfaces on the forward or interior surface of section 110 that supports the patient's leg, which otherwise may irritate or even cause sores on the leg. In addition, the smooth and streamlined exterior or back surface of section 110 helps to prevent injury or irritation to the other leg of the patient. Often, a patient wearing the splint will cross his or her legs while immobilized in bed or otherwise bring their legs in contact. Protrusions present on the back surface of certain prior art devices can injure or irritate the patient's leg. Thus, the present invention overcomes this disadvantage.

Depending upon the circumstances, it may be desirable to keep a patient's foot or leg from rotating in either direction by the use of an abductor bar 123 that can be fastened onto lateral snap-in bar 122 as shown in FIGS. 3 and 5–7 by means of bolt 133 or some other type of connector and alternative apertures 135 in the abductor and apertures 132 in the lateral snap-in bar 122. The abductor 123 can be attached to lateral snap-in bar 122 so that the abductor extends in either the same or the opposite direction as lateral snap-in bar 122. In the latter case, abductor bar 123 can extend outwardly from both sides of splint 100 to preclude rotation in either direction. The length that abductor 123 extends from lateral snap-in bar 122 can be adjusted by the selection of apertures 132 and 135.

When a patient wears a splint on each foot, a single abductor bar 123 can be fastened onto the lateral snap-in bars 122 of both splints. This arrangement serves to keep either foot from rotating, and also maintains the feet in a spaced relation to each other.

The garment assembly 200 for cushioning the patient's foot and for securing it to the shell 100 is shown in FIGS. 1 and 10–13. The garment 200 comprises a fleece-like, pile-like or other soft inner liner 210 which covers much of the patient's foot and calf or lower leg, and a canvas, twill textile or other fabric outer jacket substrate 212 which provides backing for the inner liner 210. The outer jacket 212 envelops the inner liner 210 and protects the patient's foot and the inner liner 210 from exposure to the elements and to foreign objects, provides support for the foot, and secures the foot to the shell 100. Additional canvas or twill backing or material 215 is provided over the foot portion of garment 200 in a shoe-like configuration. Material 215 provides additional support to a patient's foot secured in garment 200 to help prevent foot inversion or eversion.

The garment assembly 200 includes a back portion 236 and left- and right-side portions 232, 234. Hook and loop closures 214 such as Velcro ® are provided on the perimeter of the canvas jacket at side portions 232, 234 so that the side portions, when wrapped around the patient's foot and slightly overlapped can be secured to one another. When the garment assembly 200 is thus wrapped around the foot, the inner liner 210 forms a boot-like tube. Tabs 257 are provided on portion 232 for easy grasping to facilitate the opening and closing of garment 200. The tube is truncated at the front, however, so that the patient's toes are exposed. An aperture 226 is also provided in the garment 200 to expose the patient's heel.

In order to secure the garment assembly 200 to the shell 100, a folded flap 230 (FIGS. 1, 11 and 12) forms an envelope on the back of the jacket 212 for receiving the upper portion of the shell. The envelope may be formed using hook and loop closures such as Velcro ®, or by sewing the flap to the back of the jacket. A second envelope 231 (FIG. 1) is similarly formed at the bottom of, and adjacent to the front of, jacket 212 in order to receive a front portion of plantarsection 114. An aperture (not shown) is provided in envelope 231 to receive fastener 124. Securing straps 240 extend from the ankle portion of the material 215 around the back of heel portion 112A to meet in back of the shell 100. The straps may be secured to one another using hook and loop closures such as Velcro ®. Tightening of the straps 240 increases the range of upward pressures which are exerted by the splint to resist downward movement of the foot. An additional strap 253 located in the interior of the boot-like garment 200 can be used to secure the ankle region of a patient's foot to the shell 100 for increased stability. Strap 253 encircles the patient's instep and extends through slits 241 in heel portion 112A to meet over the patient's foot. The ends of the strap may be fastened to one another by means of hook and loop closures such as Velcro ®. An additional internal strap 255 to secure the patient's upper calf to shell 100 can also be included to encircle the upper calf region of the patient's leg and to extend through slits or openings 243 (FIGS. 2 and 3) located near the top of shell section 110. The ends of the strap may also be fastened to one another over the patient's leg by means of hook and loop closures such as Velcro ®.

The design of garment assembly 200 provides several advantages over prior art devices. By enveloping the patient's foot and lower leg in a boot-like tube which extends from the toes up around the calf, the foot and lower leg are more securely supported and held in place than in prior art devices. This arrangement provides more stability to the lower leg and foot, in order to resist unwanted curving or pulling of the foot due to contracting muscles and tendons.

In use, when a patient's foot is pulled downwardly against plantar section 114 by contracting muscles or tendons, the plantar section 114 will bend and thereby exert a pressure of at least three to six pounds per square inch, and possibly three to eight pounds per square inch, upward opposing the downward force of the foot. This range of pressure has been chosen so that the plantar section 114 will bend or give somewhat in response to the downward pressure exerted by the patient's foot, which serves to exercise the patient's muscles and tendons. This exercise feature is enhanced by the firm support provided by boot-like garment 200. Thus, the constant interaction between the new splint and the patient's foot and lower leg serve to prevent atrophy, and the resulting contraction of the patient's muscles and tendons which produces foot-drop.

This provides a significant advantage over many prior art devices which do not allow for such interactive exercise because they are either too rigid and thus do not bend significantly in response to the downward pressure of the patient's foot or are not rigid enough and thus do not exert sufficient upward counter-pressure to resist the downward movement of the foot. For example, U.S. Pat. No. 3,976,059 teaches that a foot splint should exert 30 to 50 pounds of pressure per square inch upwardly against a patient's foot. Under typical conditions encountered in foot-drop, the lower foot portion of the '059 patent device will not bend or give significantly in response to the downward force exerted by a patient's foot. In fact, if 30 to 50 pounds of pressure per square inch were exerted upward against a patient's foot, tissue in the foot and lower leg might be injured.

Those who are skilled in the art will readily perceive how to modify the invention. Therefore, the appended claims should be construed to cover all equivalent structures which fall within the true scope and spirit of the invention.

The claimed invention is:

1. A flexible foot splint comprising:
a unitary shell having an upright curved leg section and a curved foot section that extends substantially perpendicular to said leg section, the upright leg section being curved to partially embrace and support a patient's lower leg and the foot section being curved to support the arch of a patent's foot;
a heel section extending between said leg and foot sections, said heel section having an upright heel portion with a flattened rear surface extending over a predetermined distance between said curved leg section and a junction, and a flattened bottom portion extending substantially perpendicular to and joining said upright portion at said junction, said bottom portion having a flattened underside surface extending a predetermined distance from said upright heel portion to said curved foot section, said upright heel portion flexing in the vicinity of said junction between said upright and bottom portions of said heel section;
and means for removably securing to said shell a patient's foot and leg.

2. The foot splint of claim 1 including toe-protector means extending from said foot section and means for adjustably securing said toe-protector means to said foot section so that said toe-protector may be secured in a plurality of positions extending from the front and either side of said foot section.

3. The foot splint of claim 2 further comprising means for removably securing said toe-protector means to said foot section.

4. The foot splint of claim 3 wherein said toe-protector has a plurality of points along the length of said toe-protector to said foot section for removably securing said toe-protector at any selected one of said plurality of points.

5. The foot splint of claim 1 wherein said leg section includes an upper edge, said upper edge being formed in a concave curve.

6. The foot splint of claim 1 wherein said shell is formed from a polycarbonate material.

7. The foot splint of claim 1 wherein said foot section exerts an upward directed force in the range of about three to six pounds per square inch responsive to a downwardly bending force applied by the patient's foot.

8. The foot splint of claim 1 wherein the means for removably securing said shell to a patient's leg and foot comprises a boot-like garment with left and right side closure edge portions having means for removably securing said side portions to each other when said edges overlap each other.

9. The foot splint of claim 8 wherein said boot-like garment has open upper and lower ends and a pocket formed at each of said ends for enclosing part of said leg section and part of said foot section, respectively.

10. The foot splint of claim 8 wherein said boot-like garment includes a strap extending from approximately the mid-section of said garment for encircling said shell in a manner that removably secures said garment to said shell.

11. The foot splint of claim 8 wherein said boot-like garment is made of a textile having an inner soft liner and an outer fabric jacket which forms a substrate for said soft liner.

12. The foot splint of claim 8 further comprising strap means for encircling said patient's foot underneath said garment in a manner that removably secures said foot to the heel section of said splint; and means for tightening and loosening said strap so that said tightening of said strap increases a force which must be exerted by a patient for downwardly bending the foot section of said shell.

13. The foot splint of claim 1 including stabilizing means associated with said splint for preventing rotation of the splint about an axis formed by the lower leg of a patient lying in a prone position while wearing said splint.

14. The foot splint of claim 13 wherein said stabilizing means comprises a stabilizer bar and means disposed on the back of said leg section for receiving and securing said bar, said bar extending outwardly from and substantially perpendicularly to said leg section.

15. The foot splint of claim 14 wherein said means for receiving and securing said bar includes a latch mechanism and said bar includes means for cooperation with said latch mechanism for securing said bar to said leg section.

16. The foot splint of claim 15 wherein said bar has a plurality of points along the length of said bar for removably securing said bar to said latch mechanism at any selected one of said plurality of points.

* * * * *